United States Patent [19]

Mardis et al.

[11] Patent Number: 5,718,841
[45] Date of Patent: Feb. 17, 1998

[54] ORGANOCLAY COMPOSITIONS MANUFACTURED WITH ORGANIC ACID DERIVED ESTER QUATERNARY AMMONIUM COMPOUNDS

[75] Inventors: Wilbur Mardis, Southampton, Pa.; José Sanchez, Tabernacle, N.J.; Henry Basson, Overijse, Belgium

[73] Assignee: Rheox, Inc., Hightstown, N.J.

[21] Appl. No.: 621,932

[22] Filed: Mar. 26, 1996

[51] Int. Cl.$^6$ .............. B01J 13/00; C07F 7/02; C08K 9/04
[52] U.S. Cl. .......... 252/309; 252/315.2; 507/910; 508/136; 510/212; 510/504; 524/447; 556/173
[58] Field of Search .............. 252/315.2, 309; 507/910; 524/447; 556/173; 510/212, 504; 508/136

[56] References Cited

U.S. PATENT DOCUMENTS

| | | | |
|---|---|---|---|
| 2,622,987 | 12/1952 | Ratcliffe | 106/20 B |
| 4,022,909 | 5/1977 | Hunsucker | 510/504 X |
| 4,412,018 | 10/1983 | Finlayson et al. | 252/315.2 X |
| 4,434,075 | 2/1984 | Mardis et al. | 252/315.2 |
| 4,517,112 | 5/1985 | Mardis et al. | 252/315.2 |
| 4,585,572 | 4/1986 | Lane et al. | 252/315.2 X |
| 4,724,098 | 2/1988 | Kalz et al. | 252/315.2 |
| 5,254,271 | 10/1993 | Hamann et al. | 510/504 X |

OTHER PUBLICATIONS

South African Patent No. 92/4446 dated Jun. 17,1992 which is an English Language counterpart of German Language PCT WO 92/22622 published Jun. 9, 1992.
Derwent abstract of German Patent Application No. 4114906 published Nov. 12, 1992.
Henkel Oilfield Chemicals Brochure entitled *QMC 806 Quaternary Ammonium Compound Yellowish Paste Bearing The Date Designation,* "Edition Feb. 1993".
Henkel KGaA Material Safety Data Sheet (Draft Internal Use Only) for QMC 806 dated 1994–06–01.

*Primary Examiner*—Richard D. Lovering
*Attorney, Agent, or Firm*—Michael J. Cronin

[57] ABSTRACT

A novel organophilic clay comprising the reaction product of:

(a) a smectite-type clay; and
(b) a quaternary ammonium compound or compounds selected from the group consisting of:

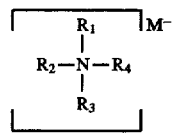

wherein $R_1$ is an unsaturated alkyl-ester group having 8 to 30 carbon atoms as described below and $R_2$, $R_3$ and $R_4$ are independently selected from the group consisting of (i) $R_1$, (ii) long chain linear or branched alkyl (including methyl), aliphatic or aromatic groups having 1 to 30 carbon atoms (such groups can also include hydroxylated groups); (iii) aralkyl groups, which are benzyl and substituted benzyl moieties, including such groups having fused ring moieties having linear chains or branches of 1 to 30 carbon atoms; (iv) aryl groups such as phenyl and substituted phenyl including fused ring aromatic substituents; (v) beta, gamma unsaturated groups having six or less carbon atoms or hydroxyalkyl groups having 2 to 6 carbon atoms; and (vi) hydrogen and $M^-$ is an anion selected from the group consisting of chloride, methylsulfate, acetate, iodide and bromide.

The organophilic clay is used in a non-aqueous fluid system such as paints, inks, and coatings to provide improved rheological properties.

12 Claims, No Drawings

ORGANOCLAY COMPOSITIONS MANUFACTURED WITH ORGANIC ACID DERIVED ESTER QUATERNARY AMMONIUM COMPOUNDS

BACKGROUND OF THE INVENTION

1. Brief Description of the Field of the Invention:

The present invention relates to novel organophilic clay compositions (hereafter "organoclay" or "organophilic clays") which are dispersible in organic or solvent-based i.e. non-aqueous, fluids to provide a wide variety of rheological and viscosity-modifier properties to such fluids. These fluids include oil-based paints and coatings as well as oil-based inks, drilling fluids, caulks and adhesives. The invention also pertains to a process for preparing these novel organophilic clays. The invention also includes organic fluid compositions including such organophilic clays as rheological additives.

2. Description of the Prior Art:

It has been known since shortly after the Second World War that organophilic clays are useful to thicken a variety of organic liquid compositions. Organophilic clays are modified smectite-type clays prepared by the reaction of an organic cation, usually a quaternary ammonium chloride compound produced from a fatty nitrile, with a smectite-type clay utilizing various processes known in the art. Smectite clays, while dispersible in water, are not dispersible in organic fluids. If the organic cation contains at least one fatty acid group containing 10 or more, preferably 12 or more, carbon atoms, such reaction-product organoclays possess the ability of dispersing into, and increasing the viscosity of, organic liquids. Organoclays, over the last fifty years, have found a large market providing thickening or rheological properties to an increasingly wide variety of such liquids including paints, coatings, inks, adhesives and similar products.

Representative U.S. Pat. No. 4,664,820, issued to the assignee hereof, describes the preparation of organophilic clays, some of which have become commercial products, that are used to thicken organic compositions. It is also well known that such organoclays may function to thicken both polar or non-polar solvents, depending on the substitutents on the organic cation. For purposes of this patent, organic and solvent are used to mean essentially the same thing. Dr. J. W. Jordan, a former senior scientist employed by the assignee hereof, in "Proceedings of the 10th National Conference on Clays and Clay Minerals" (1963), discusses a wide range of applications of organoclays from high polarity organic liquids to low polarity solvent liquids.

More recently, organophilic clay gellants have been developed which are the reaction products of smectite-type clays with certain organic cations or mixtures of organic cations, and organic anions or anion combinations. These organoclays have the advantage of being easily dispersible in particular types of organic and solvent compositions without the need for a dispersion aids or polar activators under normal factory dispersion conditions. Illustrative patents which describe such improved organophilic clays are U.S. Pat. Nos. 4,105,578; 4,208,218; 4,412,018 (issued to one of the coinventors of the instant invention); U.S. Pat. No. 4,450,095; and 4,517,112.

Recent U.S. patents issued to assignee hereof show various uses of organoclays and processing improvements in making such organoclays using conventional nitrile quaternary ammonium compounds. These patents include U.S. Pat. Nos. 4,695,402; 4,929,644; 5,034,136; 5,075,033; and 5,151,155. See also U.S. Pat. No. 5,336,647 and U.S. Pat. No. 5,429,999. U.S. Pat. No. 5,336,647 in some length details the constituents of specific quaternary compounds useful in making commercial organoclays known as of its filing date.

Quaternary ammonium compounds produced from fatty nitriles have their major use as fabric softeners and in laundry operations. In many European countries, the fact that these uses have come under environmental attack has indirectly resulted in decreasing capacity and limited available supplies. The manufacturers of nitrile-based quaternary compounds have chosen to reduce capacity by closing selected plants, rather than run all plants at reduced capacity utilization rates. This reduction in availability is expected to result in an increase in the price of nitrile-based quaternary compounds which will eventually become less and less available.

The disadvantages of most existing commercial organoclay compositions for non-aqueous systems include (a) they require the use of nitrile-processed quaternary ammonium chloride compounds, which are increasingly becoming in short supply; and (b) such organoclay compositions lack the biodegradable characteristic which is desired by more and more customers Biodegradability of the constituents of drilling fluids, particularly those used in ocean oil drilling, including organoclays contained in such fluids, is becoming a requirement of purchasers of such fluids. Organoclays are an important and essential ingredient in almost all drilling fluids based on oil chemistry. Beyond drilling fluids, almost all organoclays used in contact with the environment, such as those used in cosmetics or household products, increasingly must be biodegradable by either law or customer desire.

SUMMARY OF THE INVENTION

A new type of organophilic clay has been discovered in which the quaternary ammonium compound used to make the organoclay is made in part from organic acid-derived esters. These organoclays show in a number of circumstances either increased efficiency or substantially equivalent performance versus conventional prior art organoclays, and they can be made with quaternary compounds of either present, or anticipated, lower cost. These novel organoclays have a different structure with increased x-ray diffraction pattern $d_{001}$ spacings. The manufacture of these organophilic clays eliminate the need to use nitrile quaternaries of the type which European environmental authorities have found to be environmentally unfriendly. The present invention provides an improved, more biodegradable organophilic clay for gelling or thickening non-aqueous organic and solvent-based compositions.

Thus, according to one aspect of the invention, an organophilic clay is provided which comprises the reaction product of:

(a) a smectite-type clay having a cation exchange capacity of at least about 75 milliequivalents per 100 grams of clay, 100% active clay basis;

b) one or more organic cations in an amount sufficient to satisfy at least about 75% of the cation exchange capacity of the smectite-type clay, and of any optional organic anion(s), wherein the cation or cations are quaternary ammonium compound(s) derived from organic acid-derived esters; and optionally (c) one or more organic anion(s) that are capable of reacting with the organic cation(s) to form an organic cation/organic anion ion pair complex which is intercalated with the clay.

The present invention also contemplates a process for preparing an organophilic clay which comprises:

(a) preparing an aqueous slurry of a smectite-type clay having a cation exchange capacity of at least about 75 milliequivalents per 100 grams of clay, 100% active clay basis;

(b) heating the slurry to a temperature between about 20° C. and 100° C.;

(c) adding to the slurry;
   (i) one or more organic cation(s) derived from organic acid - derived esters; and optionally
   (ii) one or more organic anion(s) that are capable of reacting with the organic cation(s) to form an organic cation/organic anion pair which is intercalated with the clay;

(d) reacting the resulting mixture for a sufficient time to form an organophilic clay; and (e) recovering the organophilic clay.

The invention also provides non-aqueous organic compositions thickened with the above-indicated organophilic clay. A third aspect of the invention therefore relates to a non-aqueous fluid system which comprises:

(a) a non-aqueous composition; and b) an organophilic clay comprising the reaction product of:
   (i) a smectite-type clay having a cation exchange capacity of at least about 75 milliequivalents per 100 grams of clay, 100% active clay basis;
   (ii) one or more organic cation(s) in an amount sufficient to satisfy at least about 75% of the cation exchange capacity of the smectite-type clay and of any optional organic anion(s), which are derived from organic acid - derived esters; and optionally
   (iii) one or more organic anions that are capable of reacting with the clay and/or the organic cation(s) to form the above described complex.

DESCRIPTION OF THE PREFERRED EMBODIMENTS

As stated above, one aspect of the present invention relates to improved, more efficient organophilic clays. These organophilic clays are prepared by reacting a smectite-type clay with an organic cation or cations provided by specific quaternary ammonium compounds.

The clays used to prepare the organophilic clay of this invention are cation-exchangeable smectite clays which have a cation exchange capacity of about 75 or greater milliequivalents per 100 grams of clay, 100 percent active basis (i.e. beneficiated and essentially free of non-clay impurities). Smectite-type clays are well known in science, geology and in the art of rheological additives, and are commercially available from a variety of sources both in the United States and throughout the world. They are unique among clays in that they exhibit the phenomena of swelling to many times their size when contacted with water.

Chemical formula descriptions of such natural smectite clays useful in accordance with the present invention are as follows:

Montmorillonite

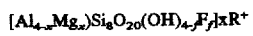

where $0.55 \leq 1.10$, $f \leq 4$ and R is selected from the group consisting of Na, Li, $NH_4$, and mixtures thereof;
Hectorite

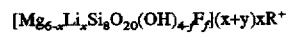

where $0.57 \leq x \leq 1.15$, $f \leq 4$ and R is selected from the group consisting of Na, Li, $NH_4$, and mixtures thereof;
Bentonite

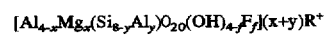

where $0 < x < 1.10$, $0 < y < 1.10$, $0.55 \leq (x+y) \leq 1.10$, $f \leq 4$ and R is selected from the group consisting of Na, Li, $NH_4$ and mixtures thereof;
Beidellite

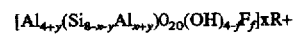

where $0.55 \leq x \leq 1.10$, $0 \leq y 0.44$, $f \leq 4$ and R is selected from the group consisting of Na, Li, $NH_4$ and mixtures thereof;
Stevensite

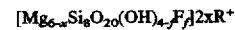

where $0.28 \leq x \leq 0.57$, $f=4$ and R is selected from the group consisting of Na, Li, $NH_4$, and mixtures thereof; and
Saponite

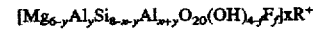

where $0.58 \leq x \leq 1.18$, $0 \leq y \leq 0.66$, $f \leq 4$ and R is selected from the group consisting of Na, Li, $NH_4$, and mixtures thereof.

Types of clays considered applicable for best practice in the present invention can also be grouped in general as three-layer types (sheet structures composed of two layers of silica tetrahedrons and one central dodecahedral or trioctahedral) as follows:

1. Expanding lattice clays.
   a. Equidimensional smectite-type clays, including montmorillonite and bentonite.
   b. Elongated smectite clays including saponite.
2. Nonexpanding lattice clays including mixed-layer types (ordered stacking of alternate layers of different types);
3. Some clays which by their generic reference fit into more than one of the above-described classification groups. "Generic reference" clays all have the common characteristics of mineral containing aluminum silicate: the major examples are 1) bentonite, and 2) hectorite.

Cation-exchangeable clays can also be synthesized usually from a montmorillonite base clay, so as to possess certain chemical and physical characteristics in order to make such clays valuable in the practice of the present invention.

The above-described clays, especially the bentonite-type clays, are preferably converted to the sodium form if they are not already in this form. Commercially important representatives of such smectite clays used to make the organoclays of this invention are sodium and calcium bentonite and hectorite. The cation exchange capacity of these smectite-type clays can be determined by the well-known methylene blue method or the ammonium acetate method. Smectite-type clays prepared synthetically by either a pneumatolytic or, preferably, a hydrothermal synthesis process may also be used to prepare the novel products of this invention.

The most preferred clays used in the present invention are Wyoming bentonite, particularly sodium bentonite, and hectorite from Hector, Calif. in the Mojave Desert. Bentonite and hectorite clays have high bonding power and react easily with the specific organic quaternary compounds described hereafter.

In addition, it will be understood that the above listed smectite-type clays which have been subjected to the application of shear may also be used to make the organoclays of the instant invention. To achieve shearing of the smectite-type clay, the clay is typically dispersed in water at a concentration of from about 0.5 to about 80% by weight. The slurry may optionally be first centrifuged to remove non-clay impurities which constitute about 10% to about 50% of the starting clay composition. Of course, if in some cases the clay has previously been treated, such as by the clay vendor, to remove such impurities, the clay as purchased without centrifuging can be formed into a slurry and subjected to shear conditions.

Shear can be imparted to the smectite-type clay slurry by means of commercially available equipment that is known to impart high shear to the material. Illustrative of such equipment are a Manton-Gaulin Homogenizer available from the APV Gaulin Company, a Tekmar SD-45 Homogenizer, a Sharples Super Centrifuge available from Sharples Division of Pennwalt Corporation, an Oakes mill available from Oakes Machinery, a Microfluidizer available from Microfluidics, a division of Biotechnology Corporation, and similar devices which can impart high laminar and turbulent shear to the clay slurry. Exemplary conditions using a Manton-Gaulin homogenizer are a pressure in the range from about 500 to about 8,000 psi with one or more passes of the clay slurry through the homogenizer. Representative processes for shearing clay slurries are described in U.S. Pat. No. 4,743,098 which is herein incorporated by reference.

The organic cations which are useful in this invention may be selected from a variety of nitrogen-based quaternary materials that are capable of exchanging cations with the selected smectite-type clay. The organic cations which are reacted with smectite type clay to prepare the inventive organophilic clays have a positive charge localized on a single nitrogen atom within the compound.

For this invention, the organic cation is provided by specific quaternary ammonium compounds derived in whole or in part from organic acid - derived esters. This organic cation is provided by a quaternary ammonium compound selected from the group consisting of the following formulae:

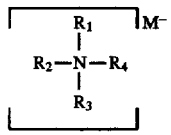

wherein $R_1$ is an alkyl or aralkyl-ester group having 8 to 30 carbon atoms as described below and $R_2$, $R_3$ and $R_4$ are independently selected from the group consisting of (i) $R_1$, (ii) long chain linear or branched alkyl (including methyl), aliphatic or aromatic groups having 1 to 30 carbon atoms (such groups can also include hydroxylareal groups); (iii) aralkyl groups, which are benzyl and substituted benzyl moieties, including such groups having fused ring moieties having linear chains or branches of 1 to 30 carbon atoms; (iv) aryl groups such as phenyl and substituted phenyl including fused ring aromatic substituents; (v) beta, gamma-unsaturated groups having six or less carbon atoms or hydroxyalkyl groups having 2 to 6 carbon atoms; and (vi) hydrogen. $M^-$ is an anion, typically chloride, methyl sulfate, acetate, iodide and bromide.

This quaternary ammonium compound must contain at least one linear or branched, saturated or unsaturated alkyl or aralkyl-ester $R_1$ group having 8 to 30 carbon atoms. Such ester groups are of the general formula:

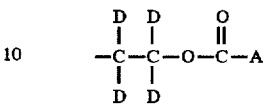

where each D is independently selected from the group consisting of H, $CH_3$ and $C_2H_5$ and A is an alkyl or aralkyl radical group.

The alkyl and aralkyl-ester groups may be derived from naturally occurring fatty oils including various vegetable oils, such as corn oil, coconut oil, soybean oil, cottonseed oil, castor oil and the like, as well as various vegetable and animal oils or fats, the most common of which are coconut oil, soyabean oil and tallow oil (obtained mostly from beef sources). These groups may likewise be synthesized from petrochemical feedstocks such as alpha olefins.

Useful organic ester-derived quaternary ammonium compounds for making the organoclays of this invention include ester quaternary compounds sold by Fina Corporation, hydrogenated tallow ester quaternaries sold by KAO Chemical Company under the tradename Tetranyl including Tetranyl AHT-2 and Tetranyl ACHF 2 and coco ester quaternaries also sold by KAO Corporation under the tradename Quartamin including Quartamin AHT-2 and Quartamin ACHF-2. These quaternaries and similar useful quaternaries made by both these companies, and by other companies, have the general formula:

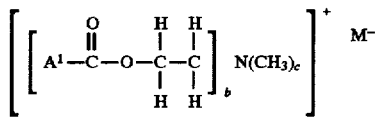

where $A^1$ represents alkyl radicals of either hydrogenated tallow or coconut fatty acids; b and c are 1, 2 or 3 and the total of b and c is always 4; $M^-$ is either chloride or methylsulfate.

Particularly preferred for this invention are dimethyl dialkyl-ester quaternary compounds.

Representative examples of useful branched alkyl groups include 12-methylstearyl and 12-ethylstearyl. Representative examples of useful branched unsaturated groups include 12-methyloleyl and 12-ethyloleyl. Representative examples of unbranched saturated groups include lauryl; stearyl; tridecyl; myristyl; tetradecyl; pentadecyl; hexadecyl and docosanyl. Representative examples of unbranched, unsaturated and unsubstituted groups include oleyl, linoleyl, linolenyl, soya, coconut and tallow. It is to be noted that natural oils such as soya; coconut and tallow are in fact mixtures of different carbon chain length elements.

Examples of aralkyl, that is benzyl and substituted benzyl moieties, include those materials derived from, e.g., benzyl halides, benzhydryl halides, trityl halides, alpha-halo-alpha-phenylalkanes wherein the alkyl chain has from 1 to 30 carbon atoms, such as 1-halo-1-phenylethane, 1-halo-1-phenylpropane, and 1-halo-1-phenyloctadecane; substituted benzyl moieties, such as those derived from ortho-, meta- and para-chlorobenzyl halides, para-methoxybenzyl halides, ortho, meta- and para-chlorobenzyl halides, para-methoxybenzyl halides, ortho-, meta- and para-nitrilobenzyl halides, and ortho-, meta- and para-alkylbenzyl halides wherein the alkyl chain contains from 1 to 30 carbon atoms; and fused ring benzyl-type moieties, such as those derived from 2-halomethylnaphthalene, 9-halomethylanthracene and 9-halomethylphenathrene, wherein the halogenated group comprises chloro-, bromo-, iodo-, or any other such group which serves as a leading group in the nucleophilic attack of the benzyl-type moiety so that the nucleophile replaces the leading group on the benzyl-type moiety.

Examples of aryl groups that are useful include phenyl and substituted phenyl, N-alkyl and N,N-dialkyl anilines, wherein the alkyl groups contain between 1 and 30 carbon atoms; ortho-, meta- and para-nitrophenyl, ortho-, meta- and para-alkyl phenyl, wherein the alkyl group contains between 1 and 30 carbon atoms, 2-, 3-, and 4-halophenyl wherein the halo group is defined as chloro-, bromo-, or iodo-, and 2-, 3-, and 4-carboxyphenyl and esters thereof, where the alcohol of the ester is derived from an alkyl alcohol, wherein the alkyl group contains between 1 and 30 carbon atoms, aryl such as a phenol, or aralkyl such as benzyl alcohols; fused ring aryl moieties such as naphthalene, anthracene, and phenanthrene.

Beta, gamma-unsaturated alkyl groups which may be included in organic cation component of the organophilic clay gellants of the invention may be selected from a wide range of materials well known in the art. These compounds may be cyclic or acyclic, unsubstituted or substituted with aliphatic radicals containing up to 3 carbon atoms such that the total number of aliphatic carbons on the beta, gamma-unsaturated radical is 6 or less. The beta, gamma unsaturated alkyl radical may be substituted with an aromatic ring that likewise is conjugated with the unsaturated beta, gamma moiety or the beta, gamma radical may be substituted with both aliphatic radicals and aromatic rings.

A representative examples of beta, gamma-unsaturated alkyl groups include 2-cyclohexenyl. Representative examples of acyclic beta, gamma-unsaturated alkyl groups containing 6 or less carbon atoms include propargyl; allyl (2-propenyl); crotyl (2-butenyl); 2-pentenyl; 2-hexenyl; 3-methyl-2-butenyl; 3-methyl-2-pentenyl; 2,3-dimethyl-2-butenyl; 1,1-dimethyl-2-propenyl; 1,2-dimethyl propenyl; 2,4-pentadienyl; and 2,4-hexadienyl. Representative examples of acyclic-aromatic substituted compounds include cinnamyl(3-phenyl-2 propenyl): 2-phenyl-2-propenyl; and 3-(4-methoxyphenyl)-2-propenyl. Representative examples of aromatic and aliphatic substituted materials include 3-phenyl-2-cyclohexenyl; 3-phenyl-2-cyclopentenyl; 1, 1-dimethyl-3-phenylpropenyl; 1,1,2-trimethyl-3-phenyl-2-propenyl; 2,3-dimethyl-3-phenyl-2-propenyl; 3,3-dimethyl-2-phenyl-2-propenyl; and 3-phenyl-2-butenyl.

Hydroxyalkyl groups may be selected from a hydroxyl substituted aliphatic radical wherein the hydroxyl is not substituted at the carbon atom adjacent to the positively charged atom; the group has from 2 to 6 aliphatic carbon atoms. The alkyl group may be substituted with an aromatic ring independently from the 2 to 6 aliphatic carbons. Representative examples include 2-hydroxyethyl; 3-hydroxypropyl; 4-hydroxypentyl; 6-hydroxyhexyl; 2-hydroxypropyl; 2-hydroxybutyl; 2-hydroxypentyl; 2-hydroxyhexyl; 2-hydroxycyclohexyl; 3-hydroxycyclohexyl; 4-hydroxycyclohexyl; 2-hydroxycyclopentyl; 3-hydroxycyclopentyl; 2-methyl-2-hydroxypropyl; 1,1,2-trimethyl-2 -hydroxypropyl; 2 -phenyl-2 -phenyl-2-hydroxyethyl; 3-methyl-2-hydroxybutyl; and 5-hydroxy-2-pentenyl.

The groups found to be most effective in producing the organic ester-derived quaternary ammonium compounds of the type found useful in this invention, in addition to one or more $R_1$ organic acid-derived ester groups of the type described are, (a) one or more methyl groups, (b) one or more benzyl groups, (c) one or more long chain alkyl groups, and combinations thereof. Most preferred $R_1$ groups are those derived from coconut oil. Specific quaternaries found most useful are dicoco esters of dimethyl diethanol ammonium chloride.

A broad variety of quaternary ammonium compounds are disclosed in U.S. Pat. No. 4,141,841 issued to Proctor & Gamble Company—see also U.S. Pat. No. 3,862,058 also issued to Proctor & Gamble.

The preparation of quaternary compounds used to make organophilic clays of this invention can be achieved by techniques well-known in the art. For example, when preparing a quaternary ammonium compound of the type described, one skilled in the art may begin with a readily available tertiary alkanolamine, such as triethanolamine, methyl or ethyl diethanolamine, dimethyl or diethyl ethanolamine, methyl or ethyl dipropanolamine, or dimethyl or diethyl propanolamine, which may be reacted with one or more fatty acids under esterification reaction conditions; the practitioner will recognize that the molar ratio of fatty acid that react with the hydroxyl moieties of the alkanol amine preferably should be at most 1:1, and can be less than 1:1. When the ratio is less than 1:1, then the resulting ester groups will be statistically distributed among the alkanol groups. If, on the other hand, the ratio of fatty acid to alkanol moieties is greater than 1:1, some amount of the fatty acid will remain unesterified following the esterification reaction, which amount may or may not have some small adverse effect on subsequent reactions of the product of this reaction.

Following the esterification of some of all of the hydroxyl moieties of the alkanol groups of the tertiary amine, the reaction product may, optionally, be reduced with a diluent, typically water and/or a low molecular weight alcohol such as methanol, ethanol, 2-propanol or butanol, and reacted with an alkylating agent under conditions well known to one skilled in the art to form the quaternary ammonium compounds useful in making the organoclays of this invention.

The organic anion(s) optionally employed in the products of the invention may be selected from a wide range of materials that are capable of reacting with the organic cations in order to form an organic cation/organic anion complex. The molecular weight of the organic anion is preferably 3,000 or less, and more preferably 1,000 or less, and contains at least one anionic moiety per molecule so as to permit the formation of the organic cation/organic anion complex which then becomes intercalated between the clay platelets.

Preferred organic anions are derived from carboxylic acids, such as stearic acid, oleic acid, palmitic acid, succinic acid, tartaric acid, etc.; sulfonic acids; and alkyl sulfates, such as the lauryl half ester of sulfuric acid and mixtures thereof.

The organic anion, which may include mixtures of organic anions, is reacted with the organic cation and smectite-type clay to form the desired organophilic clay gellant. The organic anion may be added to the reaction mixture in acid or salt form. Exemplary of the latter form are alkali metal salts, alkaline earth salts, ammonium and organic amines.

Representative salts of the organic anion are those formed with hydrogen, lithium, sodium, potassium, magnesium, calcium, barium, ammonium and organic amines such as ethanolmine, diethanolamine, triethanolamine, methyldiethanolamine, butyldiethanolamine, diethylamine, dimethylamine, triethylamine, dibutylamine, and so forth, and mixtures thereof. The most preferred salt form is with sodium.

The amount of organic anion optionally reacted with the smectite-type clay and the organic cation must be sufficient to obtain a milliequivalent ratio of organic cations to organic anion in the range of from about 1.70:1.0 to about 50:1.0, preferably from about 3.0:1.0 to about 15:1.0. The most preferred ranges depend on the particular organic cations and optional organic anion utilized and the intended environment of use and can be determined by experimentation guided by the information set forth above. Illustrative patents which describe suitable organic anions that may be co-reacted with the organic cations and the smectite type clay in order to form the organophilic clay include commonly assigned U.S. Pat. Nos. 4,412,018 and 4,434,075.

The present invention also contemplates a process for preparing an organophilic clay gellant using the specified quaternary compounds.

The organophilic clays of this invention may be prepared by admixing the clay, organic cation, optional organic anion and water together, preferably at temperatures within the range from 20° to 100° C., and most preferably from 35° to 80° C. for a period of time sufficient for the organic compounds to react with the clay. The reaction is followed by filtering, washing, drying and grinding. The organic cation may be added simultaneously or at separate intervals in any order.

The clay is preferably dispersed in water at a concentration from about 1 to 80%, most preferably, from 2 to 8%. Optionally, the slurry may be centrifuged to remove non-clay impurities which may constitute about 10 to 50% of the starting clay composition.

The amount of the quaternary ammonium compound or compounds added to the smectite clay for purposes of this invention must be sufficient to impart to the clay the improved gelling and dispersion characteristics. This amount is defined as the milliequivalent ratio, which is the amount of milliequivalents (m.e.) per 100 grams of natural clay without impurities. Such ratio and its calculation are well known in the art.

The organophilic clay gellants prepared according to this invention may be used as rheological additives in non-aqueous compositions such as paints, varnishes, enamels, waxes, paint- varnish lacquer remover, oil base drilling fluids, lubricating grease, inks, polyester resins, epoxy resins, mastices, adhesives, sealants, cosmetics, detergents, and the like. The organoclay can be added to these systems by commonly known matter including medium speed dispersers, colloid mills, roller mills, and ball mills.

While not wishing to be bound by any theoretical mechanism, it is believed that organoclays of the instant invention will be biodegradable—or more properly, environmentally degraded—as a result of hydrolysis of the ester linkage of the quaternaries of the instant invention. It is well known that the reaction(s) of a quaternary ammonium chloride with a smectite-type clay to form an organoclay is an equilibrium reaction, and that, for the reaction to proceed to completion (i.e., quantitative consumption of the quaternary ammonium chloride), at least one of the moieties attached to the quaternary ammonium cation must be a long (i.e., $\geq C_8$, preferably $\geq C_{12}$) alkyl group; organoclays prepared with quaternary ammonium cations of shorter chain lengths are in equilibrium with the raw materials for the organoclay. It is believed that this dependence on alkyl chain length is due to van der Waals forces between the alkyl chain and the surface of the clay platelet; only when the van der Waals forces of attraction are greater than the solution energy of the quaternary is the quaternary quantitatively consumed in the reaction(s) to form the organoclay.

The fatty acid(s) ester(s) of the quaternary ammonium cations of the instant invention provide the required chain length to form stable organoclays. However, once the ester linkage(s) hydrolyze, the remaining quaternary cation do not possess the requisite long chain alkyl moiety; as a result, said hydrolysis product (i.e., the organoclay with a hydrolyzed ester quaternary cation) will equilibrate with its environment in which cations other than the hydrolyzed ester quaternary cation are likely to be more prevalent returning the organoclay, ultimately, to a totally inorganic form. The quaternary ammonium cation released from the hydrolyzed ester quaternary organoclay may further degrade by other mechanisms.

The organoclays of this invention can be used in combination with other materials including organoclays made with conventional prior art quaternary compounds. Consequently, the invention also provides non-aqueous organic and solvent compositions thickened with the above-indicated organophilic clay gellant. Thus, a third aspect of the invention relates to a non-aqueous fluid system which comprises:

(a) a non-aqueous liquid composition such as paint, coatings, drilling fluids, ink or similar materials; and an organophilic clay gellant comprising the reaction product of:

(i) a smectite-type clay having a cation exchange capacity of at least about 75 milliequivalents per 100 grams of clay, 100% active clay basis;

(ii) an organic cation or cations, as described, in an amount sufficient to satisfy at least about 75%, preferably at least 100%, of the cation exchange capacity of the smectite-type clay and of any optional organic anion(s); and optionally (iii) one or more organic anion(s) that are capable of reacting with the organic cation or cations to form a complex as described previously.

The organophilic clay complexes of the invention are added to the non-aqueous compositions in mounts sufficient to obtain the desired rheological properties. Amounts of the organophilic clay complexes in the non-aqueous compositions are from about 0.01% to 15%, preferably from about 0.3% to 5%, based on the total weight of the non-aqueous fluid system.

The following examples are given to illustrate the invention, but are not deemed to be limiting thereof. All percentages given throughout the specification are based upon weight unless otherwise indicated.

EXAMPLE 1

This example and Examples 2 to 6 illustrates the preparation of organoclays according to the present invention.

In this example, 45.00 grams of beneficiated un-sheared Wyoming bentonite clay slurry was diluted with water to form a 2% by weight dilute slurry of bentonite in water. The slurry was heated to 65° C. in a reaction flask equipped with a stirrer, thermometer and addition funnel. 28.54 grams of a dicoco ester of dimethyl diethanol ammonium methylsulphate quaternary compound, commercially available as TETRANYL ACHF-2 from Kao Corporation, was added to the clay slurry. The mixture was stirred for 30 minutes at 65° C. The product was filtered through a Buchner funnel to collect the solids. The wet solids were reslurried in 1500 grams of water at 65° C. for 20 minutes and then recollected on a Buchner funnel. The organoclay "filtercake" was dried at 45° C. for 16 hours.

EXAMPLE 2

The procedure of Example 1 was repeated, except that 34.62 grams dihydrogenated tallow ester of dimethyl diethanol ammonium methylsulphate, commercially available as TETRANYL AHT-2 from Kao Corporation was used.

COMPARATIVE EXAMPLE A

For comparative purposes, the procedure of Example 1 was repeated, except that 24.15 grams of dimethyl dihydrogenated tallow ammonium chloride, a quaternary compound commonly used to make a variety of commercial organoclays, was added.

EXAMPLES 3-6

The compositions are prepared according to the procedure of Example 1, except that additional quaternary ammonium compounds were added as described:
Example 3—dihydrogenated tallow ester of dimethyl diethanol ammonium chloride
Example 4—dihydrogenated tallow ester of methyl triethanol ammonium methylsulphate
Example 5—dicoco ester of methyl triethanol ammonium methylsulphate
Example 6—dicoco ester of dimethyl diethanol ammonium chloride

EXAMPLES 7-19

A typical organic system paint formulation was prepared according to Formulation 1.
Formulation 1
Long Oil Alkyd Paint

| Ingredients | Description | Manufacturer | Amount (Pounds) |
|---|---|---|---|
| Millbase | | | |
| Beckosol 10-060 | Long oil alkyd | Reichhold | 105.76 |
| Mineral Spirits 66/3 | Solvent | | 70.60 |
| Organoclay | | | 7.17 |
| MeOH/H2O 95/5 | Polar activator | | 2.39 |

-continued

| Ingredients | Description | Manufacturer | Amount (Pounds) |
|---|---|---|---|
| KRONOS 2101 | Titanium Dioxide | KRONOS | 325.00 |
| Letdown | | | |
| Beckosol 10-060 | Long oil alkyd | Reichhold | 445.90 |
| 6% ZR Nuxtra | Drier | Hüls | 10.30 |
| 6% Co Nuxtra | Drier | Hüls | 3.42 |
| EXKIN #2 | Anti skin agent | Hüls | 2.00 |
| Mineral spirits 66/3 | Solvent | | 54.70 |
| | | | 1027.24 |

Each of the organoclay samples prepared in Examples 1 to 6, Comparative Example A and Bentone 34, were dispersed into Formulation 1 at a loading of 0.7% using a Dispersmat disperser. B34 (Bentone 34) is a commercial organoclay made by Rheox Inc. using a nitrile quaternary derived from tallow. The results demonstrate the viscosity and other typical coating properties provided when the novel organoclays of the invention when used in an alkyd resin paint formulation. The various tests employed were standard laboratory measurements conventionally used in determining the effectiveness of organoclays in providing rheological properties to organic liquids.

Paint Properties:

| Example (Composition) | FOG | Stormer Viscosity (KU) | Brookfield 10 RPM (cP) | Viscosity 100 RPM (cP) | T.I. | Sag (Mil) | Gloss |
|---|---|---|---|---|---|---|---|
| 7 (Example 1) | 7BA | 91 | 2120 | 1264 | 1.68 | 4.8 | 90 |
| 8 (2) | 7BA | 86 | 1680 | 1040 | 1.62 | 4.2 | 91 |
| 9 (Example 3 Comp A) | 7BA | 86 | 1680 | 1088 | 1.54 | 3.9 | 94 |
| 10 (B34) | 7BA | 89 | 1800 | 1144 | 1.57 | 5.0 | 89 |
| 11 (no additive used) | 7BA | 82 | 800 | 800 | 1.00 | 3.0 | 91 |
| 12 (4) | 6C | 94 | 2100 | 1384 | 1.52 | 5 | 90 |
| 13 (5) | 6BC | 89 | 1700 | 1160 | 1.47 | 5 | 88 |
| 14 (B34) | 7AB | 94 | 2220 | 1414 | 1.57 | 5 | 89 |
| 15 (no additive used) | 7AB | 82 | 800 | 800 | 1.00 | 3 | 91 |
| 16 (3) | 7B | 91 | 2900 | 1430 | 2.03 | 5.6 | |
| 17 (6) | 7B | 86 | 2000 | 1150 | 1.74 | 4.8 | |
| 18 (B34) | 7B | 87 | 2080 | 1140 | 1.82 | 4.9 | |
| 19 (Blank) | 7B | 75 | 700 | 620 | 1.13 | 3.0 | |

Discussion of Results: Many of the above results demonstrate that organoclays made according to this invention are superior to conventional organoclays—compare examples 7 to 9 and 16 to 18. While some of the examples shown equal or slightly diminished effectiveness, all inventive examples are technically and commercially acceptable.

Based on the foregoing results, it is apparent that the organophilic clays provided by the invention are highly effective in improving the rheological properties of non-aqueous systems.

The invention thus being described, it will be obvious that the same may be varied in many ways. Such variations are not to be regarded as a departure from the spirit and scope of the invention and all such modifications are intended to be included within the scope of the claims.

What is claimed:

1. An improved organophilic clay useful in providing rheological properties to non-aqueous fluid systems comprising the reaction product of:

(a) one or more smectite-type clays having a cation exchange capacity of at least about 75 milliequivalents per 100 grams of clay, 100% clay, active clay basis; and (b) a quaternary ammonium compound or compounds derived from a organic acid-derived ester in an amount sufficient to satisfy at least 75% of the cation exchange capacity of the smectite-type clay which compound or compounds is selected from the group consisting of:

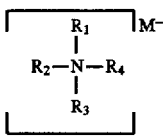

wherein $R_1$ is an alkyl-ester or aralkyl-ester group having 8 to 30 carbon atoms and $R_2$, $R_3$ and $R_4$ are independently selected from the group consisting of (i) $R_1$, (ii) linear or branched alkyl, aliphatic or aromatic groups having 1 to 30 carbon atoms (such groups can also include hydroxylated groups); (iii) aralkyl groups, which are benzyl and substituted benzyl moieties, including such groups having fused ring moieties having linear chains or branches of 1 to 30 carbon atoms; (iv) aryl groups; (v) beta, gamma-unsaturated groups having six or less carbon atoms or hydroxyalkyl groups having 2 to 6 carbon atoms; and (vi) hydrogen and $M^-$ is an anion selected from the group consisting of chloride, methyl sulfate, acetate, iodide and bromide.

2. The organophilic clay of claim 1, wherein an organic anion or anions is included in the reaction product to form a complex, and said organic anion or anions is provided by a compound selected from the group consisting of carboxylic acids, sulfonic acids, alkyl sulfates and mixtures thereof.

3. The organophilic clay of claim 1, wherein said smectite-type clay or clays is selected from the group consisting of bentonite, hectorite and mixtures thereof.

4. The organophilic clay of claim 1 wherein one or more of the quaternary ammonium compounds has the formula:

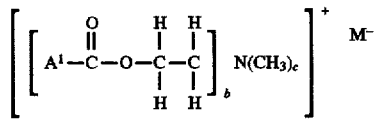

where $A^1$ represents alkyl radicals derived from the group consisting of hydrogenated tallow and coconut fatty acids; b and c are 1, 2 or 3 and the total of b and c is always 4; and $M^-$ is either chloride or methyl sulfate.

5. An improved organophilic clay useful in providing rheological properties to non-aqueous fluid systems comprising the reaction product of:

(a) one or more smectite-type clays selected from the group consisting of bentonite, hectorite and mixtures thereof having a cation exchange capacity of at least about 75 milliequivalents per 100 grams of clay, 100% clay, active clay basis; and (b) a quaternary ammonium compound or compounds derived from a organic acid-derived ester in an amount sufficient to satisfy at least 75% of the cation exchange capacity of the smectite-type clay which compound or compounds is selected from the group consisting of:

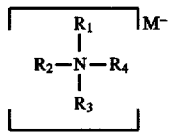

wherein $R_1$ is an alkyl-ester or aralkyl-ester group having 8 to 30 carbon atoms and $R_2$, $R_3$ and $R_4$ are independently selected from the group consisting of(i) $R_1$, (ii) linear or branched alkyl, aliphatic or aromatic groups having 1 to 30 carbon atoms (such groups can also include hydroxylated groups); (iii) aralkyl groups, which are benzyl and substituted benzyl moieties, including such groups having fused ring moieties having linear chains or branches of 1 to 30 carbon atoms; (iv) aryl groups; (v) beta, gamma-unsaturated groups having six or less carbon atoms or hydroxyalkyl groups having 2 to 6 carbon atoms; and (vi) hydrogen and $M^-$ is an anion selected from the groups consisting of chloride, methyl sulfate, acetate iodide and bromide wherein the quaternary ammonium compound contains one or more $R_1$ groups of the formula:

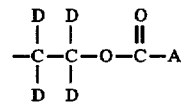

where each D independently is selected from the group consisting of H, $CH_3$ and $C_2H_5$ and A is an alkyl or aralkyl radical group which group has been derived from naturally occurring oils selected from the group consisting of coconut oil, soybean oil and tallow.

6. The organophilic clay of claim 5 wherein the quaternary ammonium compound is selected from the group consisting of a dicoco ester of dimethyl diethanol ammonium methylsulphate, a dicoco ester of methyl triethanol ammonium methylsulphate, a dicoco ester of dimethyl diethanol ammonium chloride, a dihydrogenated tallow ester of dimethyl diethanol ammonium chloride; a dihydrogenated tallow ester of methyl ammonium methylsulphate and a dihydrogenated tallow ester of dimethyl diethanol ammonium methylsulfate.

7. A process for preparing an organophilic clay which comprises:

(a) preparing an aqueous slurry of a smectite-type clay having a cation exchange capacity of at least about 75 milliequivalents per 100 grams of 100% clay, active clay basis;

(b) heating said slurry to a temperature between about 20° C. and 100° C.;

(c) adding to said slurry a quaternary ammonium compound or compounds in an amount sufficient to satisfy at least about 75% of the cation exchange capacity of the smectite type clay selected from the group consisting of:

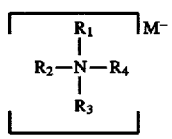

wherein $R_1$ is an alkyl-ester or aralkyl-ester group having 8 to 30 carbon atoms and $R_2$, $R_3$ and $R_4$ are independently selected from the group consisting of (i) $R_1$, (ii) linear or branched alkyl aliphatic or aromatic groups having 1 to 30 carbon atoms (such groups can also include hydroxylated groups); (iii) aralkyl groups, which are benzyl and substituted benzyl moieties, including such groups having fused ring moieties having linear chains or branches of 1 to 30 carbon atoms; (iv) aryl groups; (v) beta, gamma-unsaturated groups having six or less carbon atoms or hydroxyalkyl groups having 2 to 6 carbon atoms; and (vi) hydrogen and $M^-$ is an anion selected from the group consisting of chloride, methylsulfate, acetate, iodide and bromide, (d) reacting the resulting mixture for a sufficient time to form an organophilic clay; and (e) recovering the organophilic clay.

8. The process of claim 7 wherein one or more of the quaternary ammonium compounds has the formula:

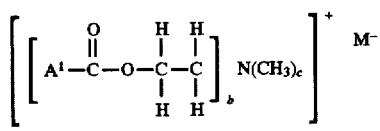

where A represents alkyl radicals derived from the group consisting of hydrogenated tallow and coconut fatty acids; b and c are 1, 2 or 3 and the total of b and c is always 4; $M^-$ is either chloride or methyl sulfate.

9. A non-aqueous fluid system comprising a non-aqueous composition and an organophilic clay which organophilic clay comprises the reaction product of: (a) a smectite-type clay having a specific cation exchange capacity of about at least 75 milliequivalent per 100 grams of clay, 100% clay, active clay basis; and (b) a quaternary ammonium compound or compounds in an amount sufficient to satisfy at least 75% of said specified cation exchange capacity selected from the group consisting of:

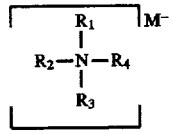

wherein $R_1$ is an alkyl-ester or aralkyl-ester group having 8 to 30 carbon atoms and $R_2$, $R_3$ and $R_4$ are independently selected from the group consisting of (i) $R_1$, (ii) linear or branched alkyl aliphatic or aromatic groups having 1 to 30 carbon atoms (such groups can also include hydroxylated groups); (iii) aralkyl groups, which are benzyl and substituted benzyl moieties, including such groups having fused ring moieties having linear chains or branches of 1 to 30 carbon atoms; (iv) aryl groups; (v) beta, gamma-unsaturated groups having six or less carbon atoms or hydroxyalkyl groups having 2 to 6 carbon atoms; and (vi) hydrogen and $M^-$ is an anion selected from the group consisting of chloride, methylsulfate, acetate, iodide and bromide.

10. The non-aqueous fluid system of claim 9 wherein one or more of the quaternary ammonium compounds has the formula:

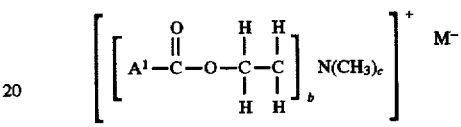

where $A^1$ represents alkyl radicals derived from the group consisting of hydrogenated tallow and coconut fatty adds; b and c are 1, 2 or 3 and the total of b and c is always 4; and $M^-$ is either chloride or methylsulfate.

11. The non-aqueous fluid system of claim 9, wherein said non-aqueous composition is selected from the group consisting of paints, varnishes, enamels, waxes, paint-varnish, lacquer remover, oil base drilling fluids, greases, inks, polyester resins, epoxy resins, mastices, adhesives, sealants, cosmetics and detergents.

12. The non-aqueous fluid system of claim 9, wherein said organophilic clay is present in an amount of about 0.01% to about 15% based on the total weight of said non-aqueous fluid system.

* * * * *